US012797502B1

(12) United States Patent
Gilreath

(10) Patent No.: US 12,797,502 B1
(45) Date of Patent: Nov. 17, 2026

(54) SAFETY-LOCK TEMPERATURE-DEPENDENT CONCENTRATED-OZONE COMPACTOR ODOR CONTROL

(71) Applicant: Chris Gilreath, Rogers, AR (US)

(72) Inventor: Chris Gilreath, Rogers, AR (US)

( * ) Notice: Subject to any disclaimer, the term of this patent is extended or adjusted under 35 U.S.C. 154(b) by 1343 days.

(21) Appl. No.: 17/546,316

(22) Filed: Dec. 9, 2021

Related U.S. Application Data

(60) Provisional application No. 63/122,975, filed on Dec. 9, 2020.

(51) Int. Cl.

| | |
|---|---|
| ***A61L 2/00*** | (2006.01) |
| ***A61L 9/015*** | (2006.01) |
| ***B02B 1/00*** | (2006.01) |
| ***B02B 5/02*** | (2006.01) |
| ***B09B 3/32*** | (2022.01) |

(52) U.S. Cl.
CPC ................ *A61L 9/015* (2013.01); *B09B 3/32* (2022.01); *A61L 2209/111* (2013.01); *A61L 2209/134* (2013.01); *A61L 2209/14* (2013.01); *A61L 2209/212* (2013.01)

(58) Field of Classification Search
CPC ... B02C 19/12; B09B 3/35; A61L 2/00; A61L 2/202; A61L 2/24; A61L 11/00; A61L 2202/15
USPC ............ 241/36, 38, 101.2; 422/32, 292, 309
See application file for complete search history.

(56) References Cited

U.S. PATENT DOCUMENTS

| | | | | |
|---|---|---|---|---|
| 4,944,220 | A | 7/1990 | Fox | 100/90 |
| 5,167,927 | A * | 12/1992 | Karlson | G01N 33/0039 374/10 |
| 6,742,448 | B1 | 6/2004 | Davis et al. | 100/34 |
| 7,550,111 | B2 | 6/2009 | Klaptchuk | 422/32 |
| 8,425,857 | B2 | 4/2013 | Glazer | 422/292 |
| 10,722,095 | B1 | 7/2020 | Gilreath et al. | |
| 10,807,891 | B1 | 10/2020 | Gilreath et al. | |
| 2020/0316660 | A1 * | 10/2020 | Jude | B09B 3/35 |

* cited by examiner

*Primary Examiner* — Monzer R Chorbaji
(74) *Attorney, Agent, or Firm* — Reisling & Pieper PLC; Trent C. Keisling; David B. Pieper

(57) ABSTRACT

An ozone odor control system for a waste compactor using a temperature modified control cycle for an ozone generator and air dispersion system combined with a timed delay access waste chute interlock.

19 Claims, 7 Drawing Sheets

Pin out circuit board

| Pin | Componet |
|---|---|
| P9 (pump) | Blower |
| P14 (fan) | Air pump |
| P4 (therm) | Thermistor |
| P8 (Ozone) | Ozone 1 |
| P15 (Ozone) | Ozone 2 |
| P3 | Piezo Button |
| P6 (LCD) | LCD Touchscreen |
| P11 (pwr in) | Power |

SAFETY-LOCK TEMPERATURE-DEPENDENT CONCENTRATED-OZONE COMPACTOR ODOR CONTROL

CROSS-REFERENCE TO RELATED APPLICATIONS

This application claims priority to and is a continuation-in-part of U.S. Patent Application Ser. No. 63/122,975, filed on Dec. 9, 2020 entitled SAFETY-LOCK TEMPERATURE-DEPENDENT CONCENTRATED-OZONE COMPACTOR ODOR CONTROL which is hereby incorporated by reference in its entirety.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention relates to improvements in odor control for disposal compactors. More particularly, the invention relates to improvements particularly suited for providing a safety-lock temperature-dependent concentrated-ozone disposal compactor odor control.

2. Description of the Known Art

As will be appreciated by those skilled in the art, the use of ozone is known in various arts. Patents disclosing information relevant to the use of ozone include: U.S. Pat. No. 4,944,220, issued to Fox on Jul. 31, 1990 entitled Trash compactor for sanitary handling of solid waste; U.S. Pat. No. 7,550,111, issued to Klaptchuk on Jun. 23, 2009 entitled Treatment of biomedical waste; and U.S. Pat. No. 8,425,857, issued to Glazer, on et al. Apr. 23, 2013 entitled System and method for processing waste material. Also of interests are U.S. Pat. No. 10,807,891, issued to Gilreath, et al. on Oct. 20, 2020 entitled Ozone circulated cleaning water apparatus and method; and U.S. Pat. No. 10,722,095, issued to Gilreath, et al. on Jul. 28, 2020 entitled Water conserving cleaning system, apparatus and method. Also known is the use of interlocks on access doors in waste compactors as illustrated by U.S. Pat. No. 6,742,448, issued to Davis et al. on Jun. 1, 2004, entitled Baler with doors and platen positions interlocks. Each of these aforementioned patents is hereby expressly incorporated by reference in their entirety.

From these prior references it may be seen that these prior art patents are very limited in their teaching and utilization, and an improved safety-lock temperature-dependent concentrated-ozone disposal compactor odor control is needed to overcome these limitations.

SUMMARY OF THE INVENTION

The present invention is directed to a waste compactor system using a timed delay controlled waste chute door interlock to control access and an ozone control system to reduce or eliminate odors associated with the waste stream while maintaining safe exposure levels for the operator. These and other objects and advantages of the present invention, along with features of novelty appurtenant thereto, will appear or become apparent by reviewing the following detailed description of the invention.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION OF THE INVENTION

Figure 1:
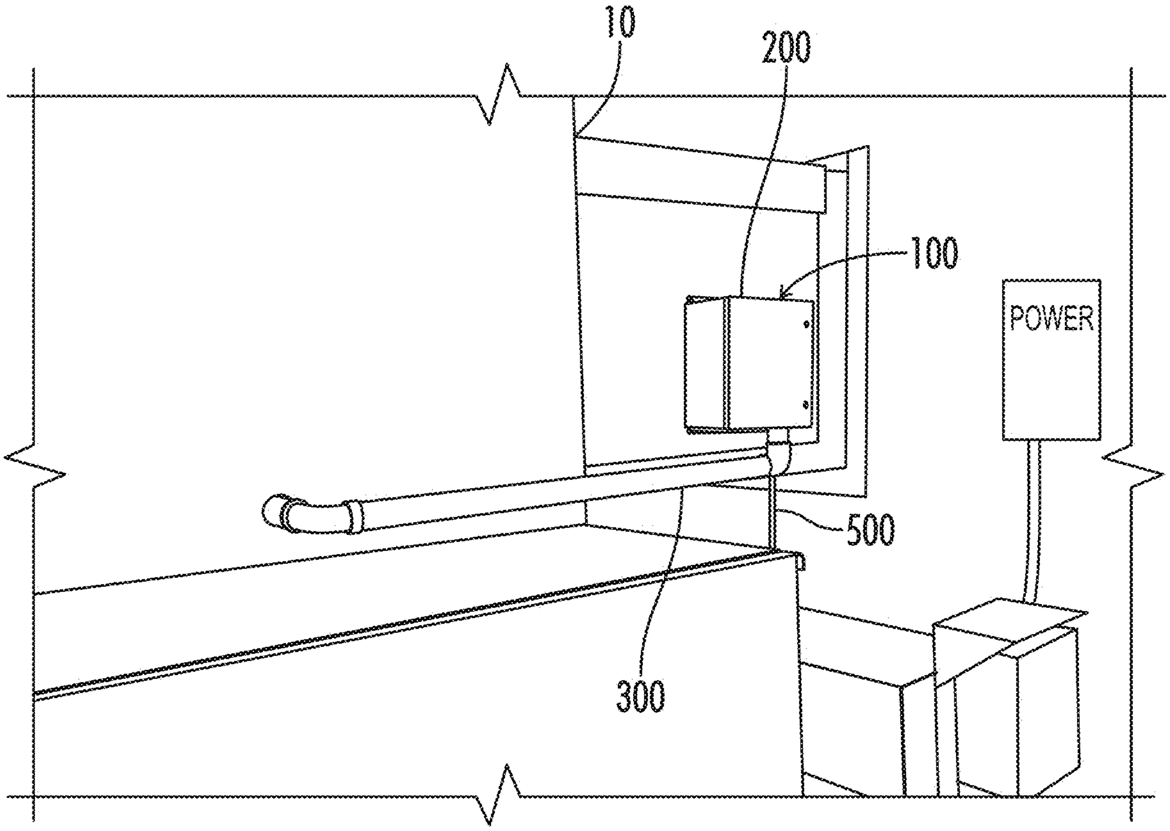
FIG. 1 is a perspective view of a safety-lock temperature-dependent concentrated-ozone disposal compactor odor control mounted on a waste compactor.
Figure 2:
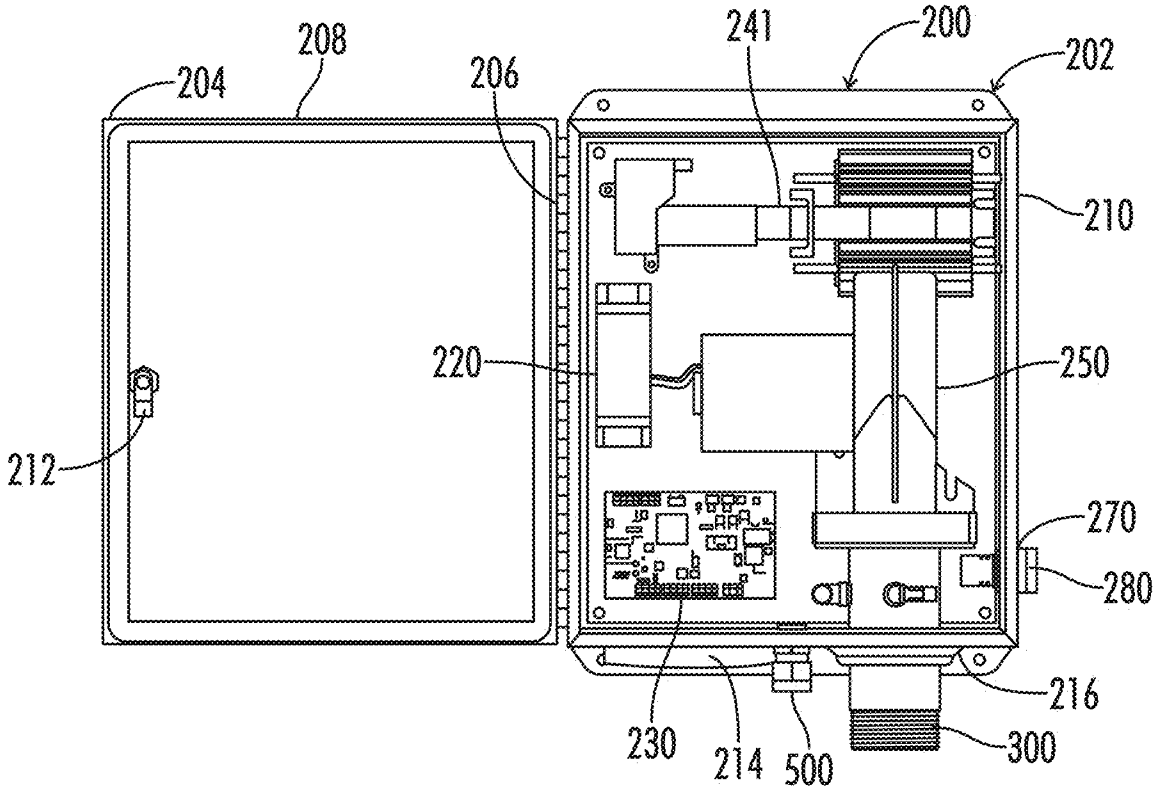
FIG. 2 is a view of the inside of the control body showing component layout.
Figure 3:
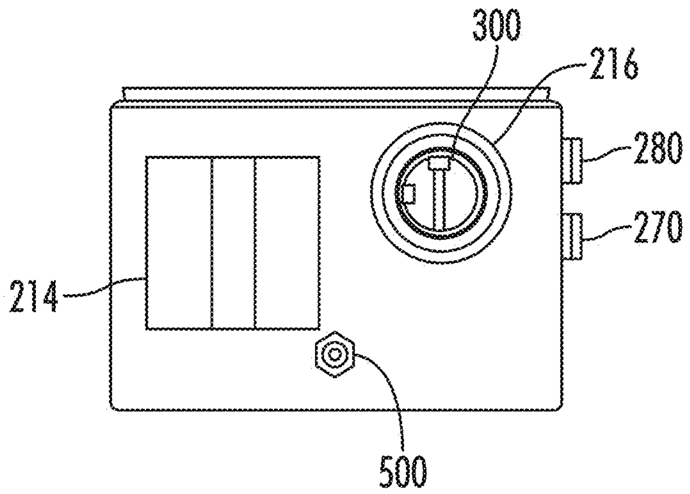
FIG. 3 is a view of the bottom of the control body.
Figure 4:
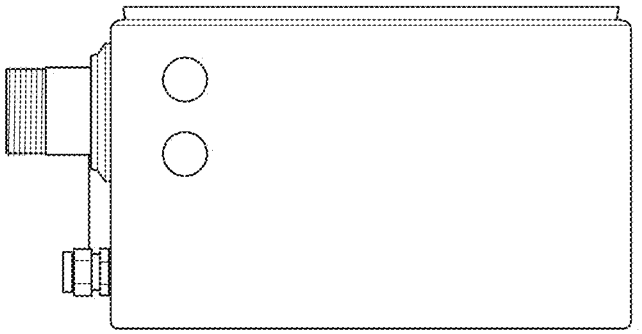
FIG. 4 is a view of the side of the control body.
Figure 5:
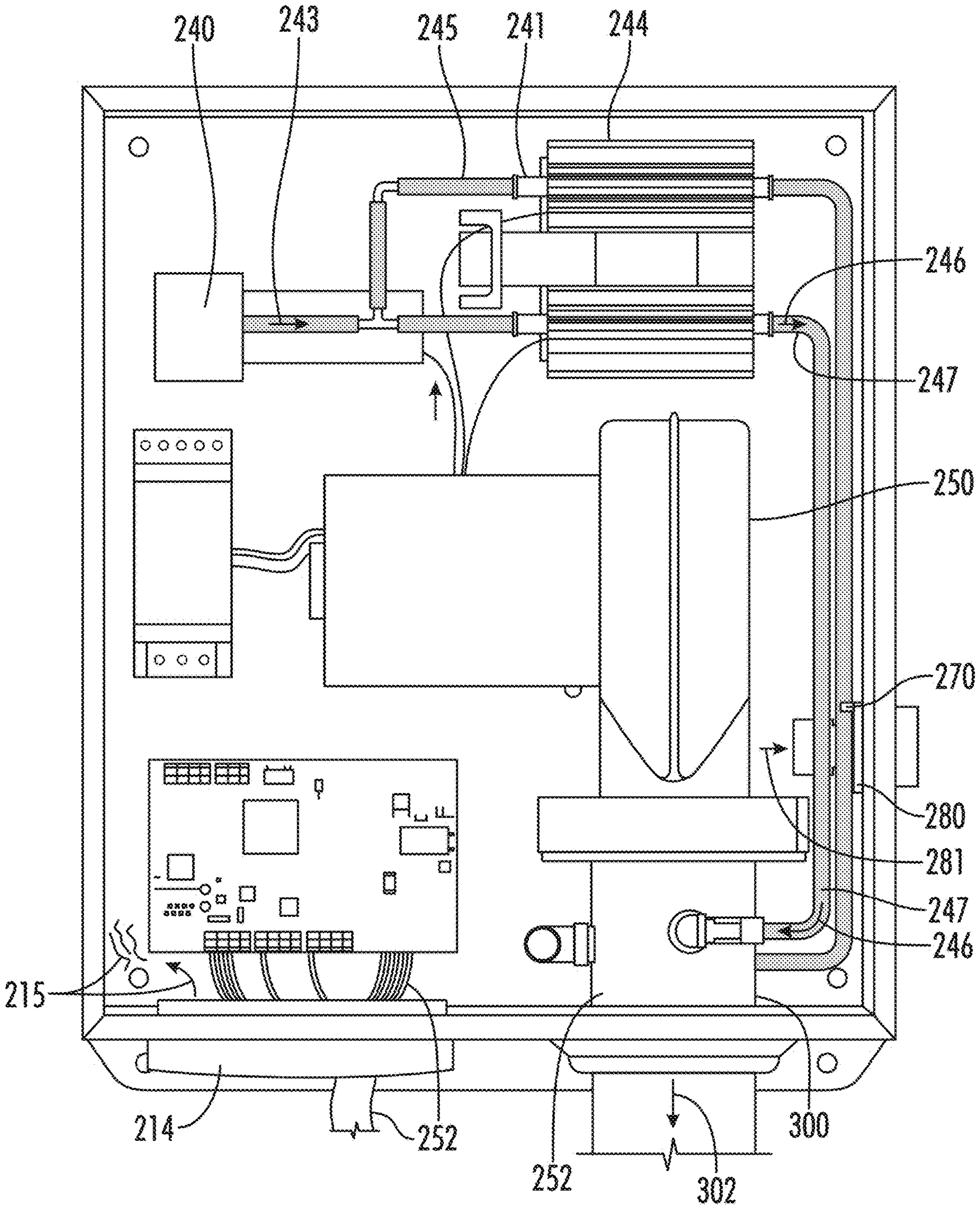
FIG. 5 is a view of the connections inside the control body.
Figure 6:
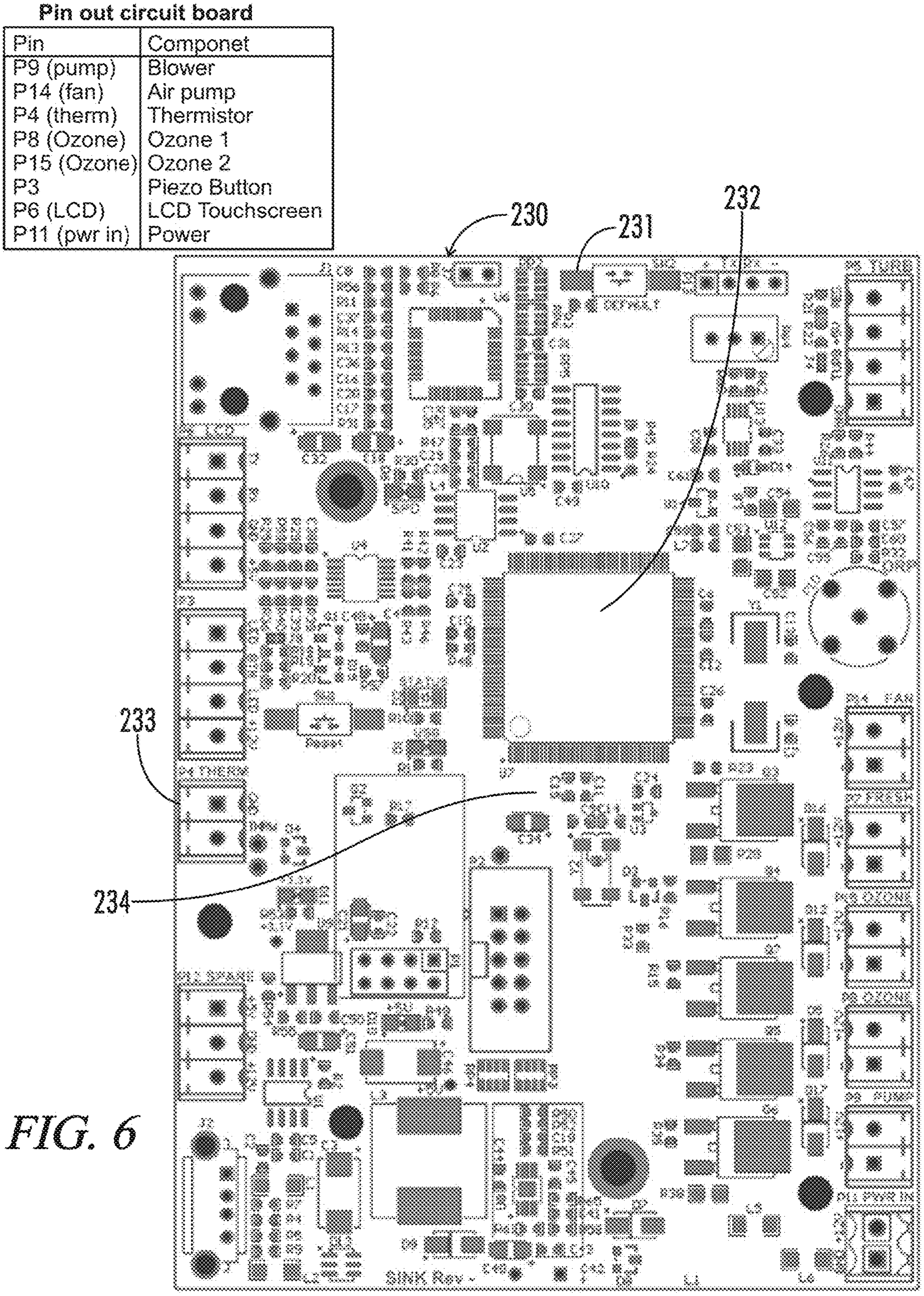
FIG. 6 is a layout of the control circuit board.
Figure 7:
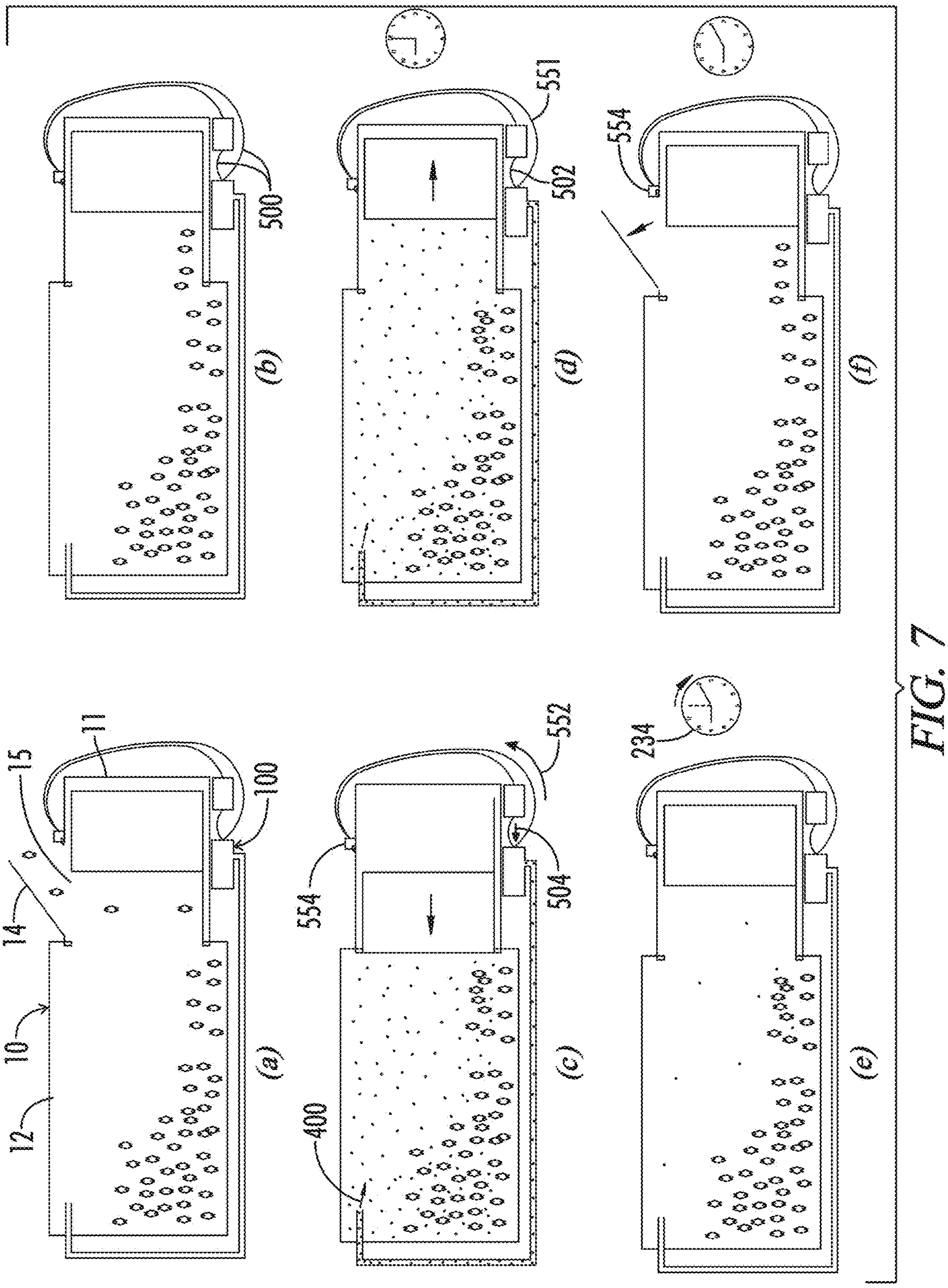
FIG. 7 is a schematic view of the operation including (a) open waste door and waste receipt, (b) system close state, (c) compaction and ozone supply, (d) ozonated state at start of dispersion, (e) timed reduction of ozone, and (f) unlocking of waste door.

As shown in FIG. 1-7 of the drawings, one exemplary embodiment of the present invention is generally shown as a safety-lock temperature-dependent concentrated-ozone disposal compactor odor control 100. The odor control 100 is applied to a disposal compactor 10 with a ram 11 compacting to a waste compaction area 12. Access to the waste chute 15 area in front of the ram 11 is provided by a waste input door 14.

The odor control 100 is constructed with control body 200, an extending ozone mixing air pipe 300 providing a temperature dependent ozonated air flow 400 to the waste compaction area 12, and an external wiring harness 500 to provide incoming power 504 and also provide an output lock control signal 552 to limit access to the waste compaction area 12 to maintain safe exposure levels for the user.

The control body 200 includes a weather resistant housing 202 with a front cover 204 mounted by a cover hinge 206 and sealed by a gasket 208 to a main cabinet 210. The front dover 204 is locked to the main cabinet 210 by a control door lock 212. The main cabinet 210 houses the power supply 220, the electronic control 230, the ozone supply 241, the air input filter 214, the air blower 250, and defines the air output port 216 for connection to the ozone mixing air pipe 300. The main cabinet 210 also provides the mounting for the control switch 270 and condition indicator 280.

The power supply 220 is a 120v to 12v power supply to power the electronics in the electronic control 230.

The electronic control 230 is implemented as an electric circuit 231 with a microprocessor 232 monitoring a thermistor temperature sensor 233 for temperature input, implementing a timer 234 for duration control, receiving a control switch signal 271 input from the control switch 270 for operation control by the user, and outputs an ozone output signal 242 for the ozone supply 241, a condition signal 281 to the visual safety condition indicator 280, and both receives a door position signal and outputs the lock control signal 552 to control the chute lock 554.

Pin Out on Sink Board

1. Blower—P9 (pump)
2. Air pump—P14 (fan)
3. Thermistor—P4 (Therm)
4. Ozone 1—P8 (Ozone)
5. Ozone 2—P15 (Ozone)
6. Piezo Button with two color (Red and Green) indicator—P3
7. LCD Touchscreen—P6 (LCD)

When activated the ozone supply 241 uses an air pump 240 to provide pressurized air 243 through pump air pipes 245 to an ozone generator 244 implemented by a pair of physical devices in the preferred embodiment. The pressurized air 243 acquires ozone in the generator to output concentrated ozone generator air 246 that is directed by generator output pipes 247 to the ozone mixing air pipe 300.

The air input filter 214 is provided to create a filtered air 215 to prevent dirt, dust, bugs, and other contaminants from entering the main cabinet 210. The filtered air 215 is pulled in by the suction created by the air blower 250.

The air blower 250 is a variable speed blower sized to coordinate with the ozone supply 241 to provide the desired concentration of ozone.

The control switch 270 and condition indicator 280 can be implemented as a two color red and green LED-piezo control switch for both sound and visual indicators as shown or can be a touch screen LCD screen or the like. When implemented as shown in the preferred embodiment the LED Indicators 280 are operated as follows:

1. Solid Green—trash chute door is unlocked and can be opened
2. Solid Red—unit is running
3. Constant Slow Blink Red—unit is in interrupt cycle waiting for timer to unlock chute door
4. 2 pulses red—Air pump failure
5. 3 pulses red—blower failure
6. 4 pulses red—time for ozone generator replacement The ozone mixing air pipe 300 is a typical pipe construction with an exterior wall and interior aperture that connects air blower output 252 form the air blower 250 and mixes it with concentrated ozone generator air 246 to form the ozonated air flow 302 to the waste compaction area 12.

The temperature dependent ozonated air flow 400 is generated by turning the ozonated air flow 302 on and off according to the following parameters in the preferred embodiment:

| Temperature °F | Cycle Hour Selection | Blower | Air-Pump Speed | Ozone Generator 1 | Ozone Generator 2 |
|---|---|---|---|---|---|
| >80 | Continuous | 100% | 100% | On | On |
| 60-79 | 2 hours on, | 100% | 100% | On | On |
| | 2 hours off | 0% | 0% | Off | Off |
| 40-59 | 1 hours on, | 100% | 100% | On | On |
| | 3 hours off | 0% | 0% | Off | Off |
| <40 | 1 hours on, | 100% | 100% | On | On |
| | 5 hours off | 0% | 0% | Off | Off |

Thus, note that the ozone generators 244 can have an extended life by using a duty cycle operation.

The external wiring harness 500 provides the input power connection 502 for the incoming power 504, and the lock control connection 551 to send the lock control signal 552 to the chute lock 554 and receive the door position signal from the chute lock 554.

Operation of the safety-lock temperature-dependent concentrated-ozone disposal compactor odor control 100 can be understood by the following sequences:

Startup Sequence:

1. Power on—Check status of operational requirements items such as the operation of the ozone generators, air movement pumps and blowers, and the position of access points such as the waste input door 14 where ozone exposure can occur to ensure safe operating conditions such as closed doors and that the waste container is in position. This can be done through the disposal controller or through the electronic control 230.
2. Air pump 240 and blower 260 turn on and trash chute lock 554 is engaged to keep door in closed position
3. 15 seconds later, ozone generator 244 turns on
4. Thermistor 233 on all time
5. Show condition indicator 280
6. Operate based on chosen duty cycle Turn Off Sequence:

1. Thermistor 233 on all time
2. Ozone generator 244 turns off
3. 90 seconds later, air pump 240 and blower 260 turn off
4. 10 minutes after ozone generators 250 turn off, change condition indicator 280 and trash chute lock 554 is disengaged Interrupt Mode: Controlled by Piezo Button Only 1. Thermistor 233 on all time
2. Ozone generator 244 turns off
3. 90 seconds later, air pump 240 and blower 260 turn off
4. Change condition indicator 280 to Red slow blink for 10 minutes after step 3, then turns solid Green and trash chute lock 554 is disengaged Data Push: Data Pushes Every Hour or Status Change 1. Date and Time
2. Software Version
3. Model Number
4. MAC address
5. Unit ID
6. Current state: On, off, air pump error, blower error
7. Total Run Time
8. Ozone run time (with hour reset option)
9. Temperature
10. Blower amperage
11. Air pump amperage Thus, it can be seen that the push button control switch 270 operation is only to interrupt the cycle for the user to put trash into the system or to remove the compacted waste. The condition indicator 280 is solid red when the system is running. When the user pushes the control switch 270 while the system is in run mode—the button indicator 280 displays a slow red blink showing that the system is in the interrupt mode. Once sufficient time has passed for the ozone to dissipate to acceptable levels, the condition indicator 280 displays a solid green. Note that this dissipations time could have already occurred because for the duty cycle, the dissipation time can be a set time from pushing the control switch 270, or the dissipation time can be calculated using the concentration of ozone, the amount of ozone supplied, time since the last supply of ozone, the open space within the waste compaction area calculated from the ram travel, the outside and internal temperatures of the waste compaction area, the leakage rate of airflow from the waste compaction area, and other factors affecting the amount and concentration of the ozone and the dissipation time. In the preferred embodiment, a simple timer is used such that unlocking occurs after the generator 244 turns off and 10 minutes pass. Then the trash compactor door 14 can be opened to receive trash or trash may be otherwise removed from the system utilizing other doors also having interlocks. The user can then push the control switch 270 while the system is in the interrupt mode to start back up or the system can detect the required operating conditions, such as all of the doors are closed, so that the system can resume operation where the condition indicator returns to a solid red.

It is also envisioned that decreased wait times for ozone dissipation in the waste compaction area 12 may be implemented by circulating the air in the waste compaction area 12 through an activated charcoal filter, exposing the ozonated air to increased temperatures, or exposing either that recirculated air or the waste compaction area 12 to ultraviolet light to break down the ozone. At this time, these additional elements to the system has not proven to be necessary, but it can be implemented where concentrations are a problem or concern such as for indoor usage.

Reference numerals used throughout the detailed description and the drawings correspond to the following elements:

- disposal compactor 10
- ram 11
- waste compaction area 12
- waste input door 14
- input chute 15
- safety-lock temperature-dependent concentrated-ozone compactor odor control 100
- control body 200
- weather resistant housing 202
- front cover 204
- cover hinge 206
- gasket 208
- main cabinet 210
- control door lock 212
- air input filter 214
- filtered air 215
- power supply 220
- electronic control 230
- electric circuit 231
- microprocessor 232
- thermistor temperature sensor 233
- timer 234
- air pump 240
- ozone supply 241
- ozone output signal 242
- pressurized air 243
- ozone generator 244
- pump air pipes 245
- concentrated ozone generator air 246
- generator output pipes 247
- air blower 250
- blower output 252
- air output port 216
- control switch 270
- control switch signal 271
- condition indicator 280
- condition signal 281
- ozone mixing air pipe 300
- ozonated air flow 302
- temperature dependent ozonated air flow 400
- external wiring harness 500
- input power connection 502
- incoming power 504
- lock control connection 551
- output lock control signal 552
- chute lock 554

From the foregoing, it will be seen that this invention well adapted to obtain all the ends and objects herein set forth, together with other advantages which are inherent to the structure. It will also be understood that certain features and subcombinations are of utility and may be employed without reference to other features and subcombinations. This is contemplated by and is within the scope of the claims. Many possible embodiments may be made of the invention without departing from the scope thereof. Therefore, it is to be understood that all matter herein set forth or shown in the accompanying drawings is to be interpreted as illustrative and not in a limiting sense.

When interpreting the claims of this application, method claims may be recognized by the explicit use of the word 'method' in the preamble of the claims and the use of the 'ing' tense of the active word. Method claims should not be interpreted to have particular steps in a particular order unless the claim element specifically refers to a previous element, a previous action, or the result of a previous action. Apparatus claims may be recognized by the use of the word 'apparatus' in the preamble of the claim and should not be interpreted to have 'means plus function language' unless the word 'means' is specifically used in the claim element. The words 'defining,' 'having,' or 'including' should be interpreted as open ended claim language that allows additional elements or structures. Finally, where the claims recite "a" or "a first" element of the equivalent thereof, such claims should be understood to include incorporation of one or more such elements, neither requiring nor excluding two or more such elements.

What is claimed is:

1. A compactor apparatus for compacting waste including a ram compacting the waste into a compaction area, the waste compaction area accessed by a user via a user accessed waste input door moving between an open door position and a closed door position, the compactor apparatus comprising:

an electronic control;

an ozone supply operatively controlled by the electronic control between an activated condition and a deactivated condition, a chute lock operatively controlled by the electronic control between a lock condition and an unlocked condition, wherein when the ozone supply is activated the chute lock is put in the lock condition to lock the user accessed waste input door in the closed position.

2. The compactor apparatus of claim 1, further comprising:

a temperature sensor outputting a temperature signal to the electronic control, and the electronic control changing the operation of the ozone supply based on the temperature signal to generate a temperature dependent ozonated air flow.

3. The compactor apparatus of claim 2, further comprising:

the temperature sensor including a thermistor.

4. The compactor apparatus of claim 1, further comprising:

control switch outputting an interrupt signal connected to the electronic control;

a timer operating for a delay time, the timer connected to the electronic control;

the electronic control receiving the interrupt signal, signaling the deactivated condition of the ozone supply, waiting the delay time, and then signaling the unlocked condition of the chute lock.

5. The compactor apparatus of claim 1, further comprising:

a condition indicator controlled by a condition signal connected to the electronic control.

6. The compactor apparatus of claim 5, further comprising:

the condition indicator signaling a failure.

7. The compactor apparatus of claim 5, further comprising:

the condition indicator signaling maintenance is needed.

8. The compactor apparatus of claim 5, further comprising:

the condition indicator signaling the chute lock is in the unlocked condition.

9. The compactor apparatus of claim 5, further comprising:

the condition indicator signaling the ozone generator is activated.

10. The compactor apparatus of claim 5, further comprising:

the condition indicator signaling pendency of the delay time.

11. The compactor apparatus of claim 1, further comprising:

a timer operating for a duty cycle time, the timer connected to the electronic control;

the electronic control receiving the duty cycle time, and signaling the activated and deactivated condition of the ozone supply based on the duty cycle time.

12. The compactor apparatus of claim 1, further comprising:

the ozone supply including an ozone generator.

13. The compactor apparatus of claim 12, further comprising:

the ozone supply including an air pump providing pressurized air to the ozone generator to generate concentrated ozone generator air.

14. The compactor apparatus of claim 13, further comprising:

an air blower connected to and move the concentrated ozone generator air.

15. The compactor apparatus of claim 14, further comprising:

the ozone supply including an air input filter providing filtered air to the air pump.

16. A compactor apparatus for compacting waste, the compactor apparatus comprising:

an extending ram compacting the waste into a compaction area;

an electronic control;

an ozone supply operatively controlled by the electronic control between an activated condition and a deactivated condition to form a duty cycle, a temperature sensor outputting a temperature signal to the electronic control, and the electronic control changing the duty cycle operation of the ozone supply based on the temperature signal to generate a temperature dependent ozonated air flow.

17. The compactor apparatus of claim 16, further comprising:

the temperature sensor including a thermistor.

18. The compactor apparatus of claim 16, the compactor apparatus further comprising:

the waste compaction area including a user accessed waste input door;

a chute lock positioned to control movement of the user accessed waste input door, the chute lock operatively controlled by the electronic control between a lock condition and an unlocked condition, a control switch outputting an interrupt signal connected to the electronic control;

a timer operating for a delay time, the timer connected to the electronic control;

the electronic control receiving the interrupt signal, signaling the deactivated condition of the ozone supply, waiting the delay time, and then signaling the unlocked condition of the chute lock.

19. The compactor apparatus of claim 16, the compactor apparatus further comprising:

the waste compaction area including a user accessed waste input door;

a chute lock positioned to control movement of the user accessed waste input door, the chute lock operatively controlled by the electronic control between a lock condition and an unlocked condition, a control switch outputting an interrupt signal connected to the electronic control;

the electronic control receiving the interrupt signal, verifying that the deactivated condition of the ozone supply has exceeded a delay time, and then signaling the unlocked condition of the chute lock.

* * * * *